(12) United States Patent
Geva

(10) Patent No.: US 11,478,196 B2
(45) Date of Patent: Oct. 25, 2022

(54) JACKET FOR MEDICAL MODULE

(71) Applicant: G-Medical Innovations Holdings Ltd., Grand Kayman (KY)

(72) Inventor: Nir Geva, Ness Ziona (IL)

(73) Assignee: G-MEDICAL INNOVATIONS HOLDINGS LTD, Grand Cayman (KY)

( * ) Notice: Subject to any disclaimer, the term of this patent is extended or adjusted under 35 U.S.C. 154(b) by 399 days.

(21) Appl. No.: 16/325,391

(22) PCT Filed: Aug. 22, 2017

(86) PCT No.: PCT/IL2017/050939
§ 371 (c)(1),
(2) Date: Feb. 14, 2019

(87) PCT Pub. No.: WO2018/037410
PCT Pub. Date: Mar. 1, 2018

(65) Prior Publication Data
US 2019/0200931 A1 Jul. 4, 2019

Related U.S. Application Data

(60) Provisional application No. 62/378,694, filed on Aug. 24, 2016.

(51) Int. Cl.
*A61B 5/00* (2006.01)
*A61B 5/0205* (2006.01)
(Continued)

(52) U.S. Cl.
CPC .......... *A61B 5/6887* (2013.01); *A61B 5/0205* (2013.01); *A61B 5/6898* (2013.01);
(Continued)

(58) Field of Classification Search
CPC ... A61B 5/6887; A61B 5/0205; A61B 5/6898; A61B 5/318; A61B 5/332;
(Continued)

(56) References Cited

U.S. PATENT DOCUMENTS 9,595,993 B1 * 3/2017 Lemmer ............... H04B 1/3888
2010/0048268 A1 * 2/2010 O'Neill ............... H04B 1/3888
455/575.8

(Continued)

OTHER PUBLICATIONS

Search report of PCT/IL2017/050939.
Written Opinion PCT/IL2017/050939.

*Primary Examiner* — Aaron F Roane
(74) *Attorney, Agent, or Firm* — Reches Patents

(57) ABSTRACT

A jacket that includes a first portion, a second portion, and an interface. The interface is movably coupled to the first portion and the second portion. The first portion comprises multiple medical modules. The multiple medical modules include at least one medical sensor and a physiological signal conduit for transferring a physiological signal from an inner side of the first portion to an exterior side of the first portion. The first and second portions are configured to be detachably coupled to a mobile phone. When the jacket is at a closed position then the first portion, the second portion and the interface define an inner space that is configured to receive the mobile phone and the first and second portions contact opposite sides of the mobile phone. When the jacket is at an open position, then only one of the first and second portions contacts the mobile phone.

24 Claims, 16 Drawing Sheets

(51) Int. Cl.
*G01K 13/20* (2021.01)
*H04B 1/3888* (2015.01)
*A61B 5/021* (2006.01)
*A61B 5/024* (2006.01)
*A61B 5/145* (2006.01)
*A61B 5/11* (2006.01)
*A61B 5/05* (2021.01)
*A61B 5/318* (2021.01)
*A61B 5/332* (2021.01)
*A61B 5/08* (2006.01)
*H04M 1/02* (2006.01)

(52) U.S. Cl.
CPC ........... *G01K 13/20* (2021.01); *H04B 1/3888* (2013.01); *A61B 5/021* (2013.01); *A61B 5/024* (2013.01); *A61B 5/02055* (2013.01); *A61B 5/02438* (2013.01); *A61B 5/05* (2013.01); *A61B 5/08* (2013.01); *A61B 5/11* (2013.01); *A61B 5/145* (2013.01); *A61B 5/318* (2021.01); *A61B 5/332* (2021.01); *A61B 5/7475* (2013.01); *A61B 2560/0431* (2013.01); *A61B 2562/0219* (2013.01); *A61B 2562/0271* (2013.01); *A61B 2562/18* (2013.01); *H04M 1/0202* (2013.01)

(58) Field of Classification Search
CPC ..... A61B 5/02055; A61B 5/021; A61B 5/024; A61B 5/02438; A61B 5/05; A61B 5/08; A61B 5/11; A61B 5/145; A61B 5/7475; A61B 2560/0431; A61B 2562/0219; A61B 2562/0271; A61B 2562/18; G01K 13/20; H04B 1/3888; H04M 1/0202
USPC ........................................................ 600/301
See application file for complete search history.

(56) References Cited

U.S. PATENT DOCUMENTS

| | | | |
|---|---|---|---|
| 2015/0263777 A1* | 9/2015 | Fraden | A61B 5/6898 455/575.8 |
| 2015/0320328 A1 | 11/2015 | Albert | |
| 2015/0338385 A1 | 11/2015 | Lee et al. | |
| 2016/0234356 A1* | 8/2016 | Thomas | H04B 1/3838 |
| 2016/0262702 A1 | 9/2016 | Cho et al. | |
| 2016/0374578 A1* | 12/2016 | Kacelenga | A61B 5/6898 600/483 |
| 2017/0079592 A1 | 3/2017 | Park | |
| 2018/0034495 A1 | 2/2018 | Kim | |

* cited by examiner

JACKET FOR MEDICAL MODULE

CROSS REFERENCE

This application claims priority from U.S. provisional patent Ser. No. 62/378,694 filing date Aug. 24, 2016, which is incorporated herein in its entirety.

BACKGROUND

There is a growing need to provide personal medical monitors.

SUMMARY

There may be provided a jacket that includes a first portion, a second portion, and an interface. The interface may be movably coupled to the first portion and the second portion. The first portion may include multiple medical modules. The multiple medical modules include at least one medical sensor and a physiological signal conduit for transferring a physiological signal from an inner side of the first portion to an exterior side of the first portion. The first and second portions may be configured to be detachably coupled to a mobile phone—accordingly the first and second portions have detachment elements (adhesive bands, loops and hooks, and the like) that enable a detachable coupling. When the jacket may be at a closed position then the first portion, the second portion and the interface define an inner space that may be configured to receive the mobile phone and the first and second portions may contact opposite sides of the mobile phone. The inner space may be configured to receive the mobile phone in the sense that the shape and size of the inner space fit or may be bigger (for example—by 5-30 degrees) to the shape and size of a mobile phone. The first and second portions may contact opposite sides of the mobile phone in the sense that the first and second portions form two opposite sidewalls of the inner space. When the jacket may be at an open position, then only one of the first and second portions may contact the mobile phone. When in an open position only one of the first and second portions forms a sidewall of the inner space.

The mobile phones may be commercially available products of predefined shapes and sizes—and the jacket may be tailored to any shape and size of the mobile phones. Non-limiting examples of mobile phones include flat and substantially rectangular shaped mobile phones that have a thickness that usually does not exceed two centimeters and have a length that may be measured diagonally between four and seven inches. Non-limiting example of mobile phones include commercially available mobile phone manufactures by Apple, Samsung, LG, Huawei, Xiomi, Nokia, Blackberry, Google, OnePlusOne, and the like.

The physiological signal conduit may be an electrode.

When the jacket is in the closed position the physiological signal conduit may contact the mobile phone.

The physiological signal conduit may include an inner surface and an outer surface, wherein an area of the outer surface may exceed an area of the inner surface, wherein when the jacket may be in the closed position the inner surface faces the inner space.

The jacket may include the physiological signal conduit and another physiological signal conduit, wherein the physiological signal conduit may include an inner surface and an outer surface, wherein the other physiological signal conduit may include another inner surface and another outer surface, wherein when the jacket may be in the closed position the inner surface and the other inner surface face the inner space.

The area of the outer surface may exceed an area of the inner surface, and an area of the other outer surface may exceed an area of the other inner surface.

The distance between the outer surface and the other outer surface may exceed a distance between the inner surface and the other inner surface.

The physiological signal conduit and the other physiological signal conduit may be coupled to one or more signals processors of the multiple medical modules.

The multiple medical modules may include a thermometer.

The multiple medical modules may include an analyzer that may be configured to analyze a medical sample conveyed on a conveyor, wherein the jacket may include slot for receiving the conveyor.

The at least one of the first and second portions may be configured to partially surround the mobile phone.

The first and second portions may be plates.

The first and second portions may include apertures that correspond to a location of images sensors of the mobile phone.

There may be provided a jacket that may include a first portion, a second portion; and an interface. The first and second portions may be movably coupled to the interface and may be configured to move between (a) a close position in which the first and second portions may be spaced apart from each other and may be ordered in a first order, and (b) an open position in which the first and second portions may contact each other and may be ordered in a second order that may be opposite to the first order. The first portion may include multiple medical modules. The first and second portions may be configured to be detachably coupled to a mobile phone. When positioned in the closed position the first portion, the second portion and the interface define an inner space that may be configured to receive a mobile phone.

At least one of the first and second portions may be configured to partially surround the mobile phone.

BRIEF DESCRIPTION OF THE FIGURES

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

DETAILED DESCRIPTION OF THE FIGURES

Figure 1:
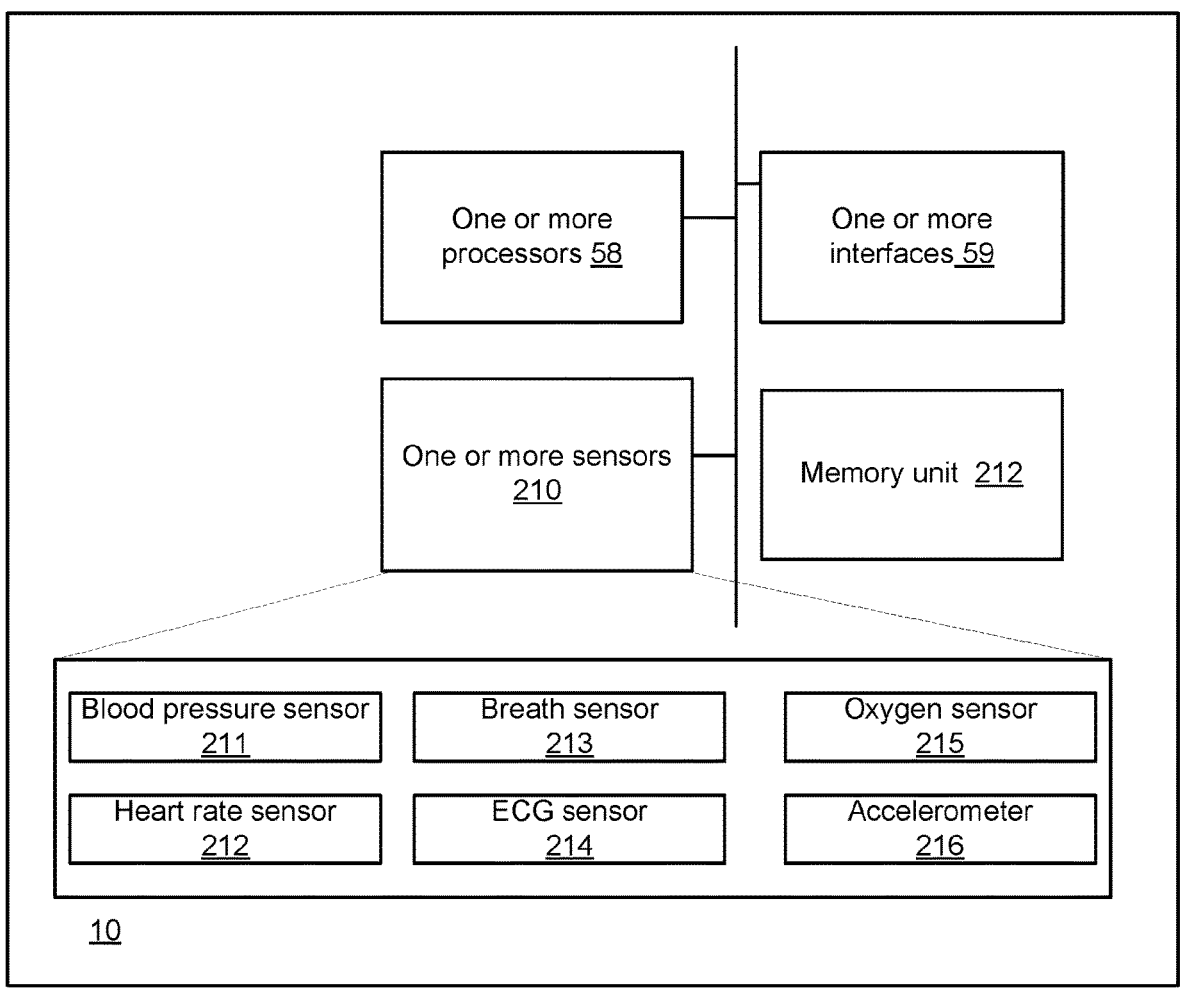
FIGS. 1-30 illustrate at least a part of a jacket that includes at least one medical module according to an embodiment of the invention.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a system capable of executing the method.

Any reference in the specification to a system should be applied mutatis mutandis to a method that may be executed by the system.

There is provided a jacket that includes one or more medical modules. The one or more medical modules may be integrated with the jacket or be detachably connected to the jacket.

The jacket may at least partially surround a smartphone.

The jacket may include a first portion (such as a rear portion) that may contact the backside of the smartphone. The first portion may allow the smartphone to be contactless charged by a wireless charger (usually by inductance)—and should not mask such contactless charging. This may be obtained by using a first portion that does is not thick (for example may be thinner than 0.5 centimeter) and is not made of inductance charging blocking materials—it may, for example be made of metal. Alternatively—the first portion may include metal parts—but the metal parts may cover only a part of the back of the smartphone—or may include apertures or include a mesh—that will enable the inductance based charging.

The jacket may include a second portion (such as a movable portion) that may face (or be proximate to) the screen of the smartphone—when the jacket is closed—thereby protecting the screen of the smartphone.

The second portion may be coupled to the first portion via an interface (also referred to as intermediate portion.

The second portion may be moved (for example by rotation or any other movement) thereby facing the first portion of the jacket (and the back of the smartphone).

The second portion may at least partially conceal the medical module. Parts of the medical module that should not be concealed (for example—sensors that should touch a person and/or have a clear field of view directed to the person) should not be permanently concealed by the second portion. Such parts may be temporarily sealed or be exposed. These parts may be exposed when the jacket is closed (not face the screen of the smartphone) or may be concealed (and may, for example, face the screen of the smartphone—when the jacket is closed. These parts may include electrodes, conductors that are electrically coupled to the electrodes, optics that follow a radiation light or precede a detector, and the like.

Concealing the medical module when the jacket is exposed may protect the medical module and also prevent any inconvenience resulting from the exposure of the medical module to the public.

Smartphones are equipped with backside cameras and other knobs, buttons or components that are positioned at the back of the smartphone. Medical devices that are permanently connected to the back of the smartphone should not cover these components and should be tailored according to the exact design of each smartphone.

Positioning the medical module within the jacket—without permanently connecting the medical module to the back of the smartphone—allows to design the medical module regardless of the exact design of the smartphone—and even allow the medical module to conceal one or more of these elements—during the medical measurement process.

The jacket in general and the second portion may include one or more chambers, one or more pockets and/or one or more compartments for holding the one or more medical modules. The one or more chambers may include one or more openings for inserting the one or more medical modules and/or for exposing parts that should be exposed, at least during a medical testing period. An opening may remain open or may be closed by any closing elements such as a zipper, or any fastening element.

The second portion can be made of plastic, of cloth, of metal and the like.

The jacket can store, in a convenient manner, more medical modules and/or medical modules of larger size than is possible by merely connecting the medical modules to the back of the smartphone.

The jacket may be detachably connected to the smartphone, may partially surround the smartphone, and the like. For example—the first portion hold the smartphone, may surround the back of the smartphone and at least a part of sidewall of the smartphone thereby connecting the jacket to the smartphone. The jacket or the first portion may be elastic and slightly smaller than the smartphone—and inserting the smartphone into the jacket or the first portion may keep the smartphone within the jacket of the first portion.

FIG. 1 illustrates a jacket that includes one or more medical modules such as but not limited to any combination of:

a. One or medical sensors (210) or one or more types (blood pressure sensor 211, heart rate sensor 212, breath sensor 213, ECG sensor 214, oxygen sensor 215, and accelerometer 216.

b. One or more interfaces 59 such as medical sensor interfaces and/or front ends (for interfacing between a sensor and a processor and/or a communication module).

c. One or more processors 58 for processing raw medical data received from a sensor, may include a communication interface for communicating with the smartphone, and the like.

d. One or more memory units such as memory unit 212 for storing sensor information, commands to be executed by the one or more sensors, and the like.

The different medical modules may be included within the jacket, in a concealed manner, in a non-concealed manner or in a partially concealed manner.

The different medical module may be connected to and/or included within and/or at least partially concealed by the first portion, the interface and/or the second portion.

Figure 2:
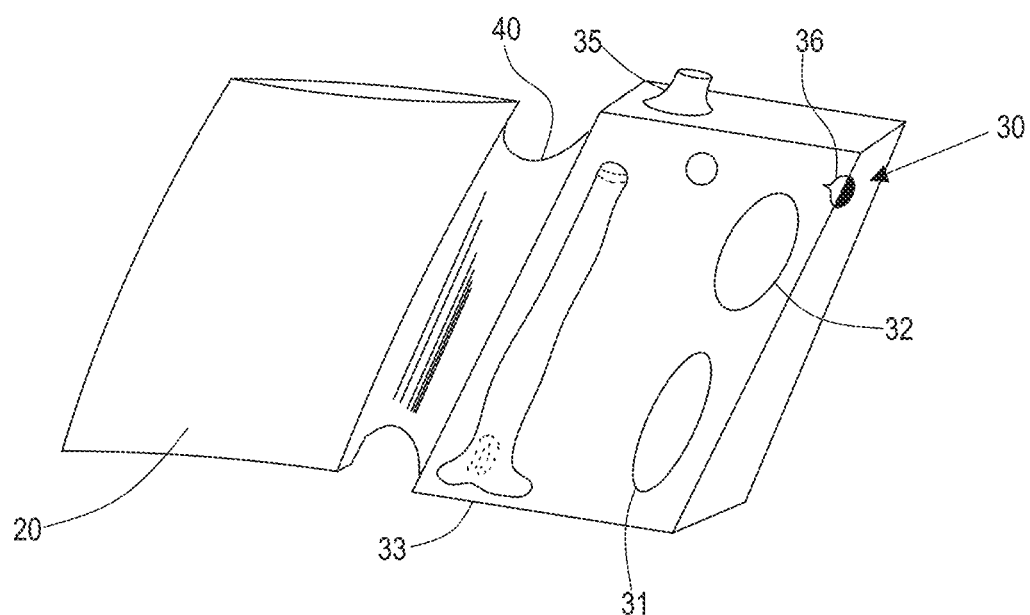

FIG. 2 illustrates the jacket 10 as including one or more medical modules such as a thermometer 35, a chemical test module that includes a slot 36 (or other opening) for insertion of strips or another sampling element that is fed to a medical module that may analyze the samples—especially analyze samples of blood or other liquid. The analysis may include conducting tests such as chemical tests—including glycose tests, hemoglobin tests, cholesterol tests and any other body liquid chemical test. The medical module that includes the slot may only partially participate in the tests There are two exposed electrodes for bio-impedance testing (ECG, fat test, heart rate, stress) and the like.

There is an aperture 33 for an optical sensor. There may be another aperture 34 for another camera or any other sensor.

Especially the first portion 20 is mechanically coupled to the second portion 30 via interface 40. In FIG. 2 the interface 40 is made of a foldable material and is connected to the entire longitudinal end of each one of the first portion 20 and the movable module.

Figure 3:
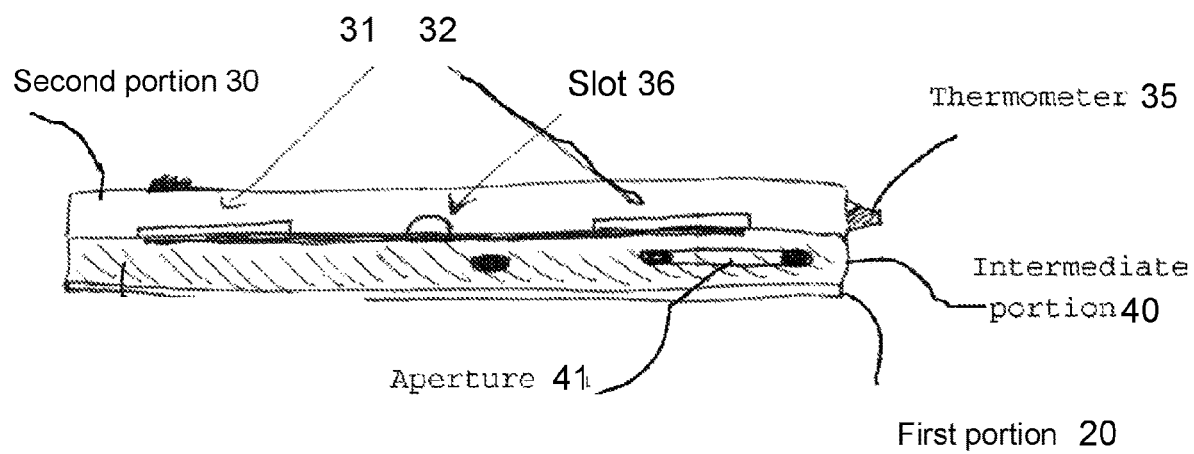

FIG. 3 illustrates a jacket at least partially surrounds a smartphone. The smartphone is concealed by interface 40 and is positioned between the second portion 30 and the first portion 20. FIG. 3 illustrates the jacket when the jacket is closed. FIG. 3 illustrates an aperture 41 formed in interface 40—for providing a clear path to a knob, button and/or sensor of the smartphone.

FIG. 3 also illustrates medical devices such as thermometer 35 and slot 36. FIG. 3 also shows electrodes 31 and 32 that are located in the second portion and are positioned to contact corresponding electrical circuits and/or electrodes of the smartphone.

Figure 4:
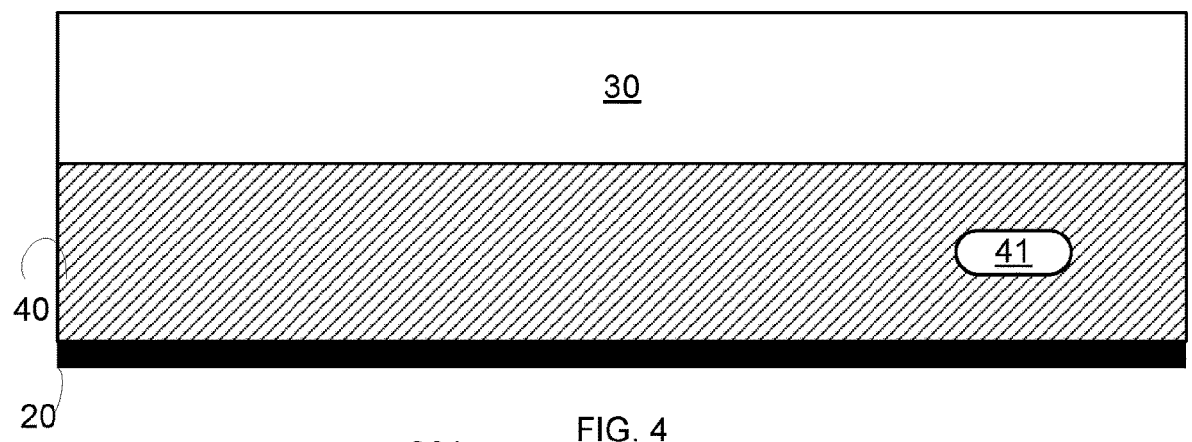

FIG. 4 is a side view of the jacket when in closed position. Second portion 30 is positioned above interface 40, and interface 40 is positioned above first portion 20. FIG. 4 also shows aperture 41. FIG. 4 illustrates a jacket at least partially surrounds a smartphone. The smartphone is concealed by interface 40 and is positioned between the second portion 30 and the first portion 20.

Figure 5:
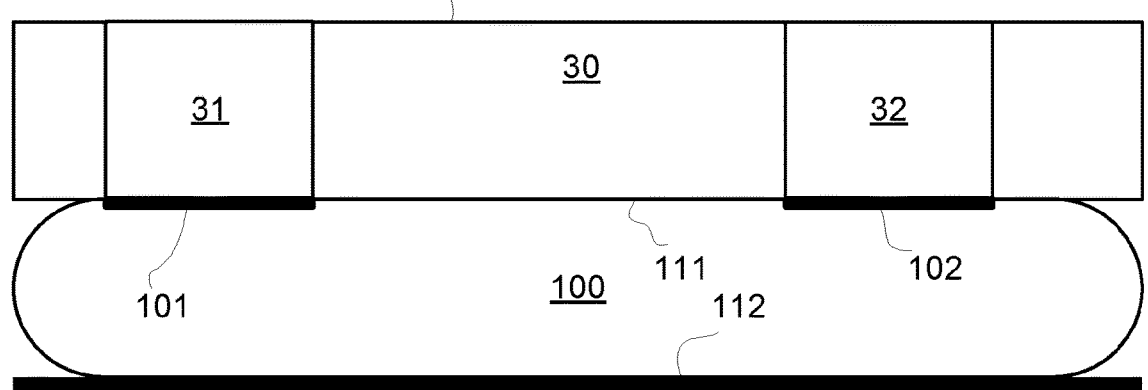

FIG. 5 is a cross sectional view of the jacket and the smartphone 100 when the jacket is closed position. First and second electrodes 31 and 32 contact electrodes 101 and 102 (respectively) of smartphone 100 and are not concealed by the front surface 301 of second portion 30. The electrodes may extend above the front surface or may be at the same height as the front surface.

Second portion 30 is positioned above interface 40, and interface 40 is positioned above first portion 20. FIG. 4 also shows aperture 41. FIG. 4 illustrates a jacket at least partially surrounds a smartphone. The smartphone is concealed by interface 40 and is positioned between the second portion 30 and the first portion 20.

In FIG. 5 the front surface 112 (for example the screen) of the smartphone faces the first portion while the back 111 of the smartphone faces the second portion 30.

Figure 6:
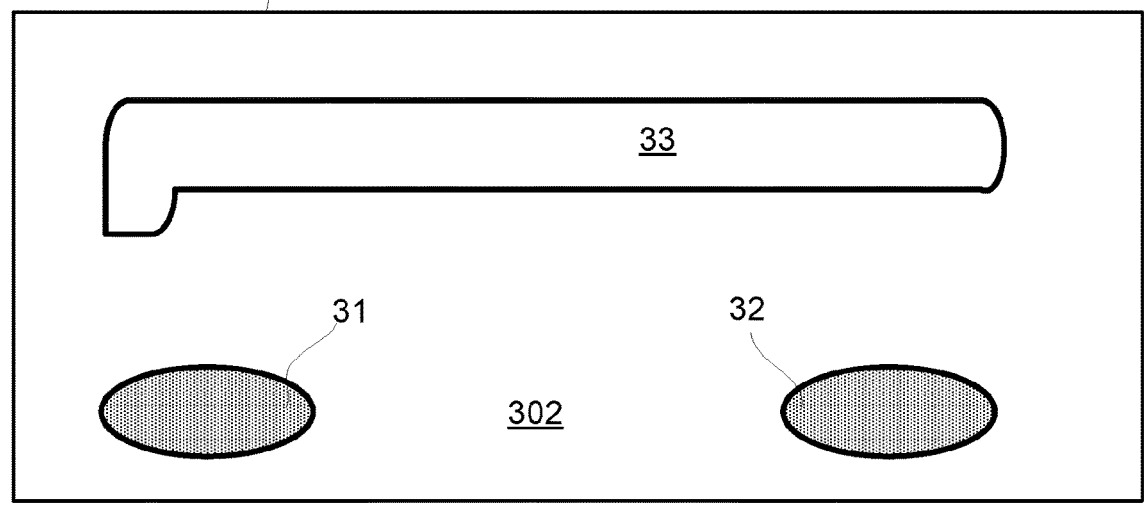

FIG. 6 is a top view of the second portion 30. The second portion has a body 302 in which electrodes 31 and 32 and aperture 33 are formed.

Figure 7:
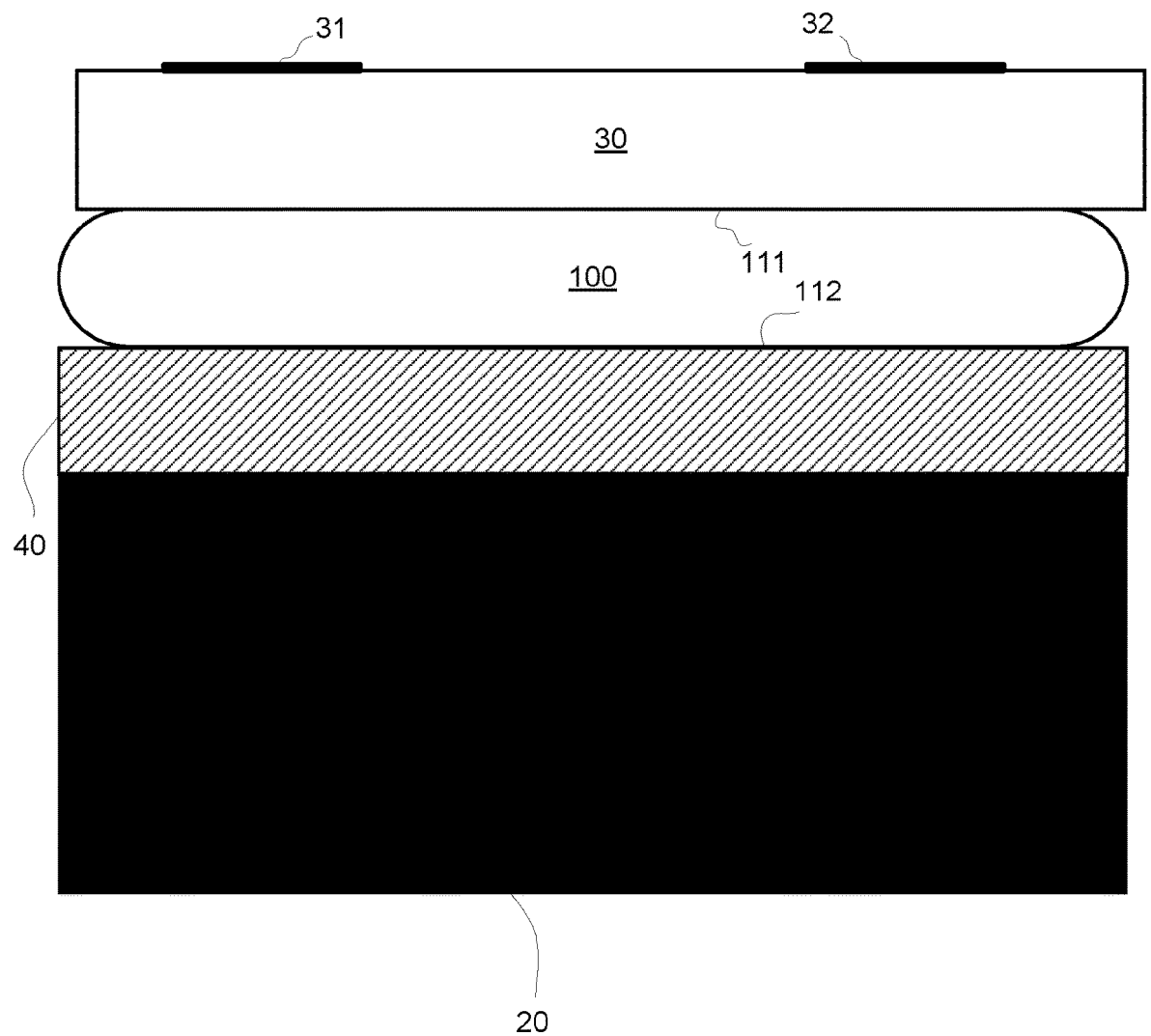

FIG. 7 is a side view of the jacket when in open position. In this position the first portion 20 and the interface 40 extend below smartphone 100 while the second portion 30 is positioned above the smartphone. In this position the user may view the screen of the smartphone and also attach the electrodes 31 and to 32 to a user for performing electrode based tests such as ECG measurements, and the like.

In FIG. 7 the front surface 112 (for example the screen) of the smartphone is above the interface and the first portion while the back 111 of the smartphone faces the second portion 30.

Figure 8:
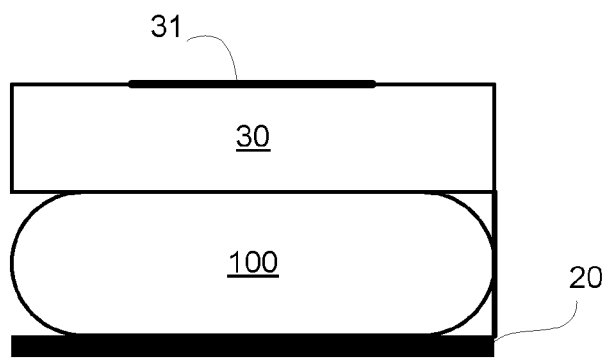

FIG. 8 is a side view (taken from the narrow dimension of the smartphone 100) when the jacket when in a closed position. FIG. 8 illustrates smartphone 100 between first portion 20 and second portion 30—and also shows electrode 31.

Figure 9:
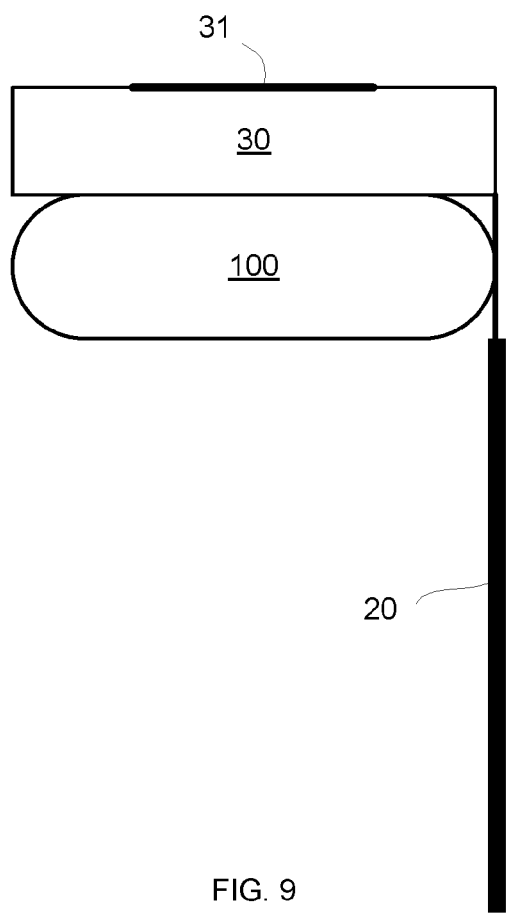
Figure 10:
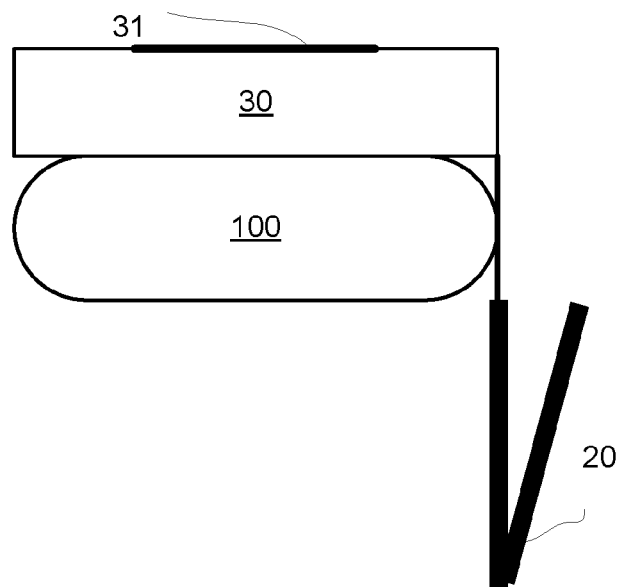
Figure 11:
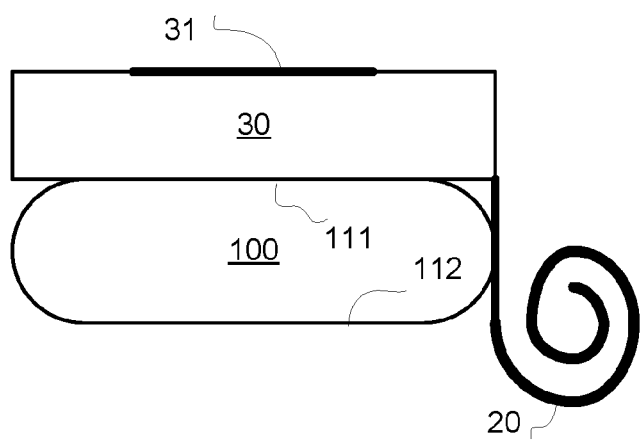

FIGS. 9-11 are a side view (taken from the narrow dimension of the smartphone 100) when the jacket when in an open position. In FIG. 9 the first portion is stretched below the interface 40. In FIG. 10 the first portion 20 is folded below the interface 40. In FIG. 11 the first portion 20 is rolled. In FIGS. 9-11 smartphone 100 is at least mostly above first portion 20 and below second portion 30. FIGS. 9-11 also show electrode 31.

Figure 12:
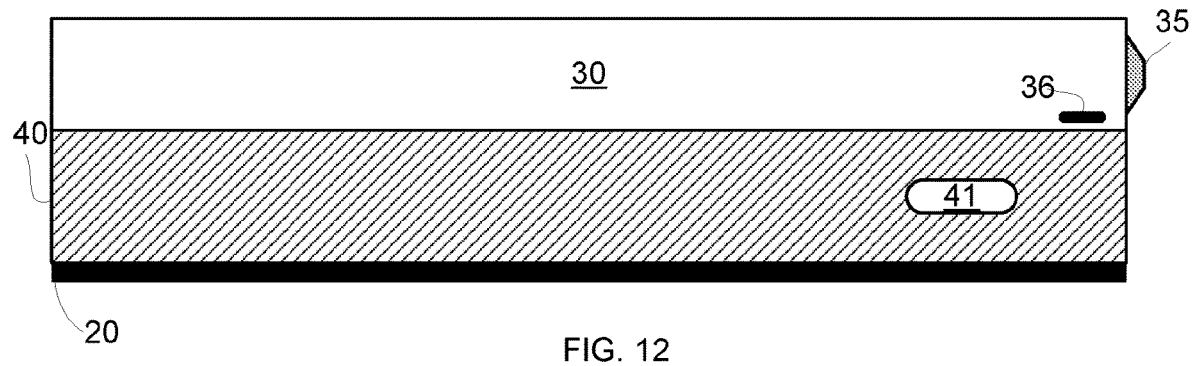

FIG. 12 is a side view of the jacket when in closed position. Second portion 30 is positioned above interface 40, and interface 40 is positioned above first portion 20. FIG. 12 also shows aperture 41. FIG. 12 illustrates a jacket at least partially surrounds a smartphone. The smartphone is concealed by interface 40 and is positioned between the second portion 30 and the first portion 20. FIG. 12 also shows thermometer 35 and slot 36.

FIGS. 13-17 are a cross sectional view of the jacket and the smartphone 100 when the jacket is closed position. For convenience only the first electrode 31 is shown. First electrode 31 contacts electrode 101 of smartphone 100 and are not concealed by the front surface of second portion 30. The electrode may extend above the front surface or may be at the same height as the front surface.

Figure 13:
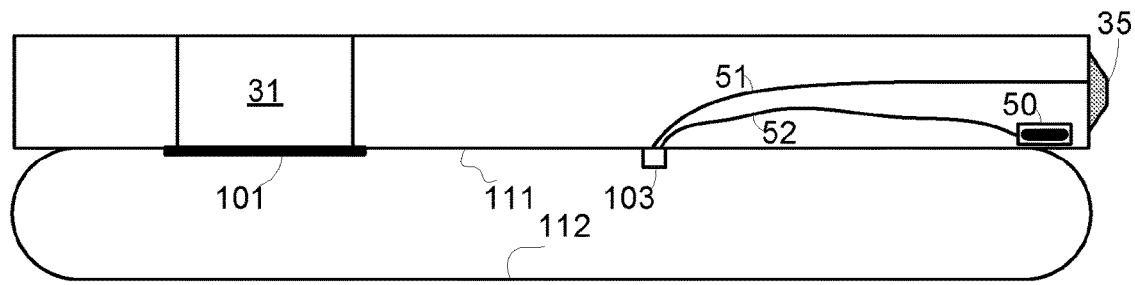

FIG. 13 also illustrates a smartphone interface 103 that is electrically coupled (via wires or groups of wires 51 and 52) to thermometer 35 and to the medical module (such as analyzer 50) that at least partially processes the samples provided via sampling elements inserted in the slot 36.

Figure 14:
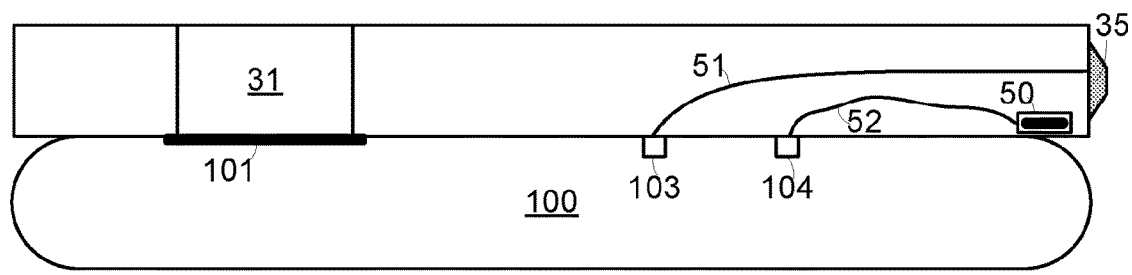

FIG. 14 also illustrates smartphone interfaces 103 and 104 that are electrically coupled (via wires or groups of wires 51 and 52) to thermometer 35 and to the medical module (such as analyzer 50), respectively. Analyzer 50 at least partially processes the samples provided via sampling elements inserted in the slot 36.

Figure 15:
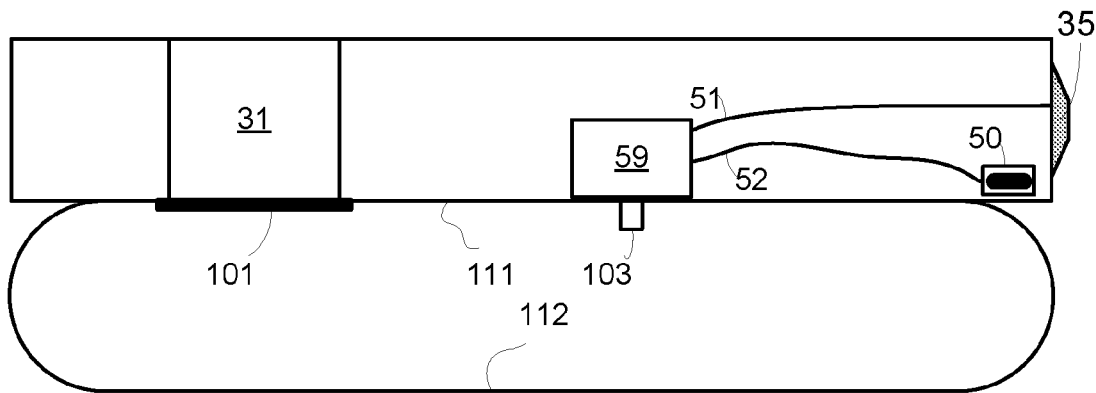

FIG. 15 also illustrates smartphone interface 103 that are electrically coupled (via wires or groups of wires 51 and 52 and via one or more interfaces 59) to thermometer 35 and to the medical module (such as analyzer 50), respectively. Analyzer 50 at least partially processes the samples provided via sampling elements inserted in the slot 36.

Figure 16:
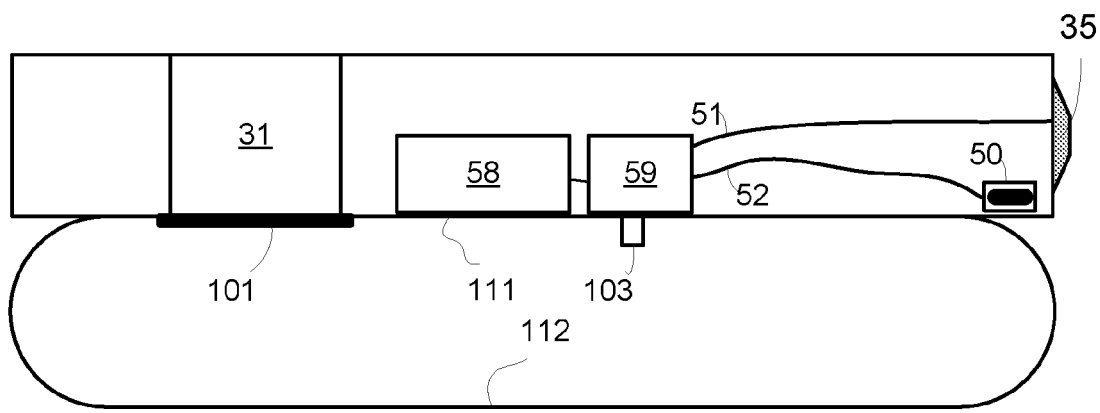

FIG. 16 also illustrates smartphone interface 103 that are electrically coupled (via wires or groups of wires 51 and 52 and via one or more interfaces 59) to thermometer 35 and to the medical module (such as analyzer 50), respectively. Analyzer 50 at least partially processes the samples provided via sampling elements inserted in the slot 36. One or more processors 58 are also coupled to the one or more interfaces 59. These one or more processors may perform various tasks such as processing detection signals, controlling one or more sensors and the like.

Figure 17:
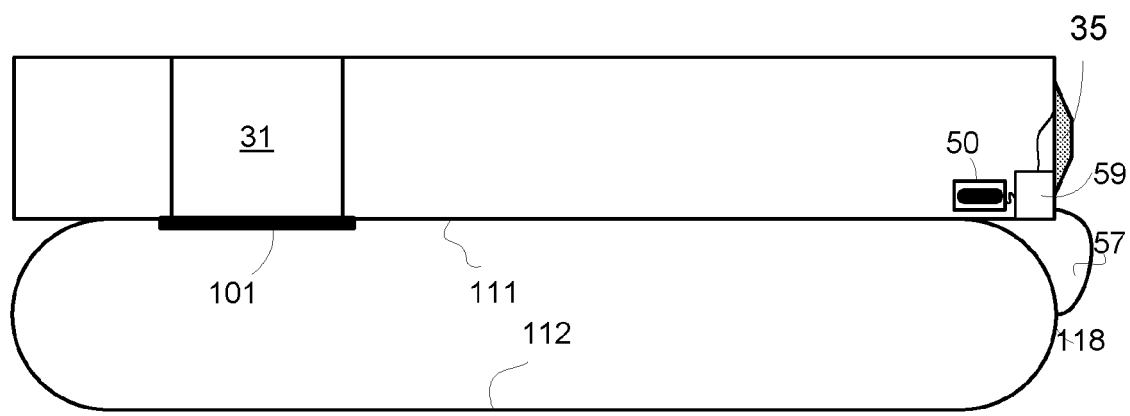

FIG. 17 also illustrates smartphone interface 118 that is coupled by wire 57 or any combination of conducting elements to one or more interface 59. The one or more interface is shown as being coupled to are electrically coupled to thermometer 35 and to analyzer 50.

Figure 18:
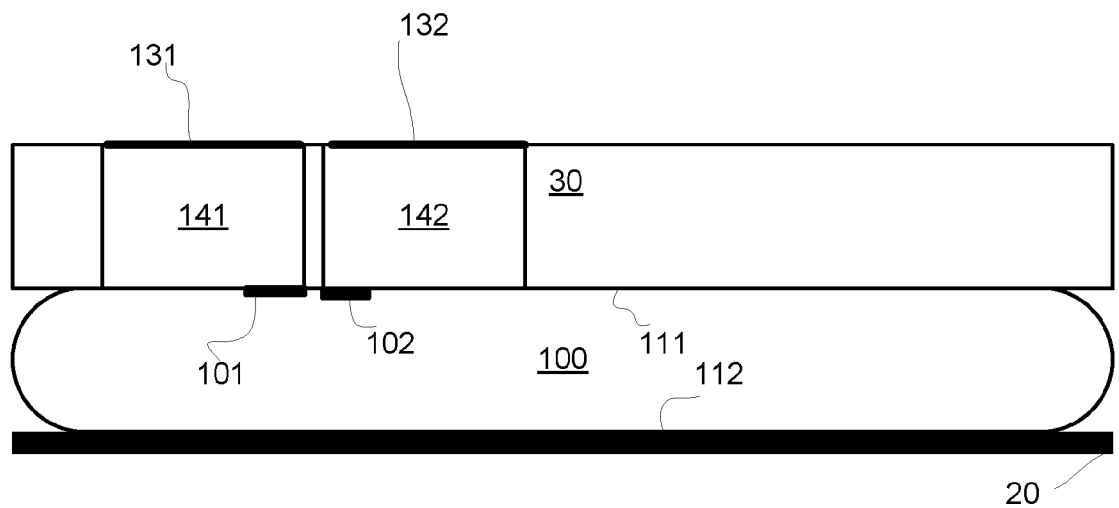
Figure 19:
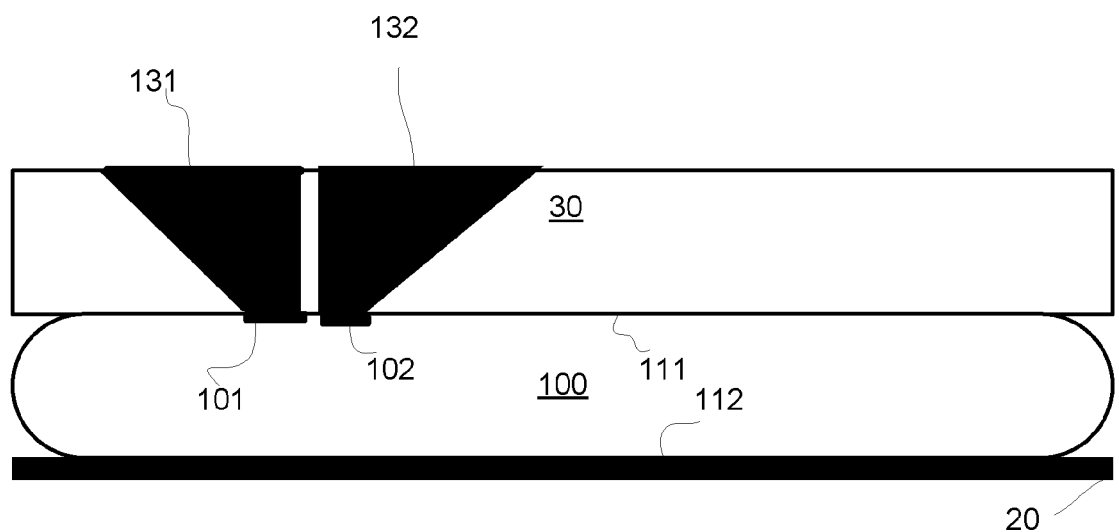

FIGS. 18-19 are cross sectional views of the jacket and the smartphone 100 when the jacket is closed position.

In FIG. 18 medical modules 141 and 142 are electrically coupled between electrodes 101 and 102, respectively and between electrodes 131 and 132. Electrodes 131 and 132 may not be concealed by other parts of the first portion—and have larger surfaces than those of electrodes 101 and 102.

The larger surface may be required in order to provide better contact with a user and/or for any other reason. Medical modules 141 and 142 may be conductors and/or may include processing circuits such as filters, processor and the like.

In FIG. 18 the conductors 131 and 131 have top surfaces that are much larger than their lower surfaces—and the top surfaces are larger than the electrodes 101 and 102 of smartphones 100. Electrodes 131 and 132 may not be concealed by other parts of the first portion—and have larger surfaces than those of electrodes 101 and 102. The larger surface may be required in order to provide better contact with a user and/or for any other reason.

Figure 20:
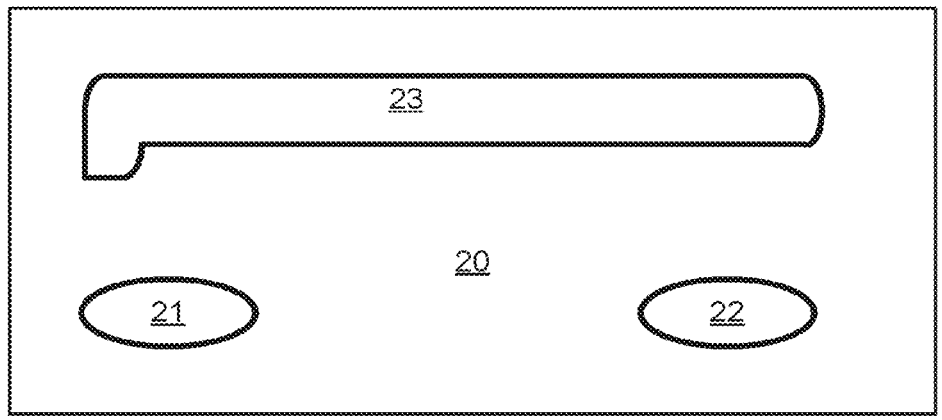
Figure 21:
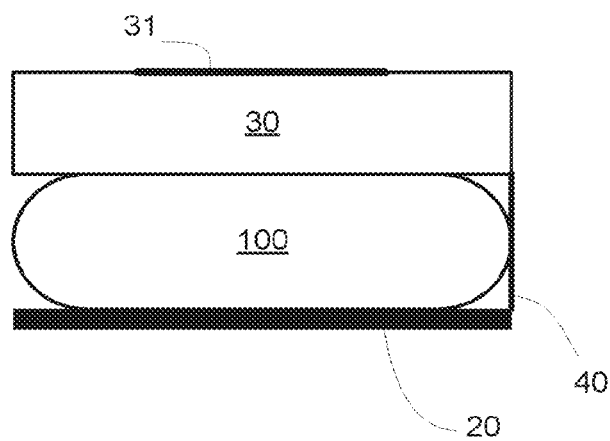

FIG. 20 is a top view of first portion 20. First portion 20 is apertures and includes apertures 21, 22 and 23 that correspond to the location of electrodes 32 and 32 and aperture 33 of second portion. In this configuration the first portion may be positioned on top of second portion without concealing first and second electrodes 31 and 32 of the second portion and without concealing aperture 33.

Figure 22:
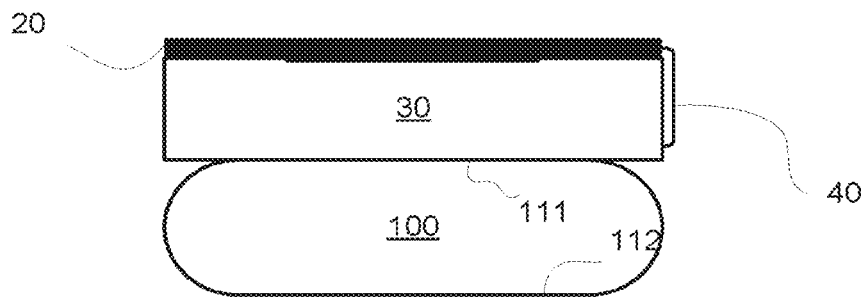

FIG. 22 is a side view (taken from the narrow dimension of the smartphone 100) of the jacket at a closed position. The smartphone 100 is positioned between the first portion 20 and the second portion 30. FIG. 22 also shows interface 40 and electrode 31.

Figure 23:
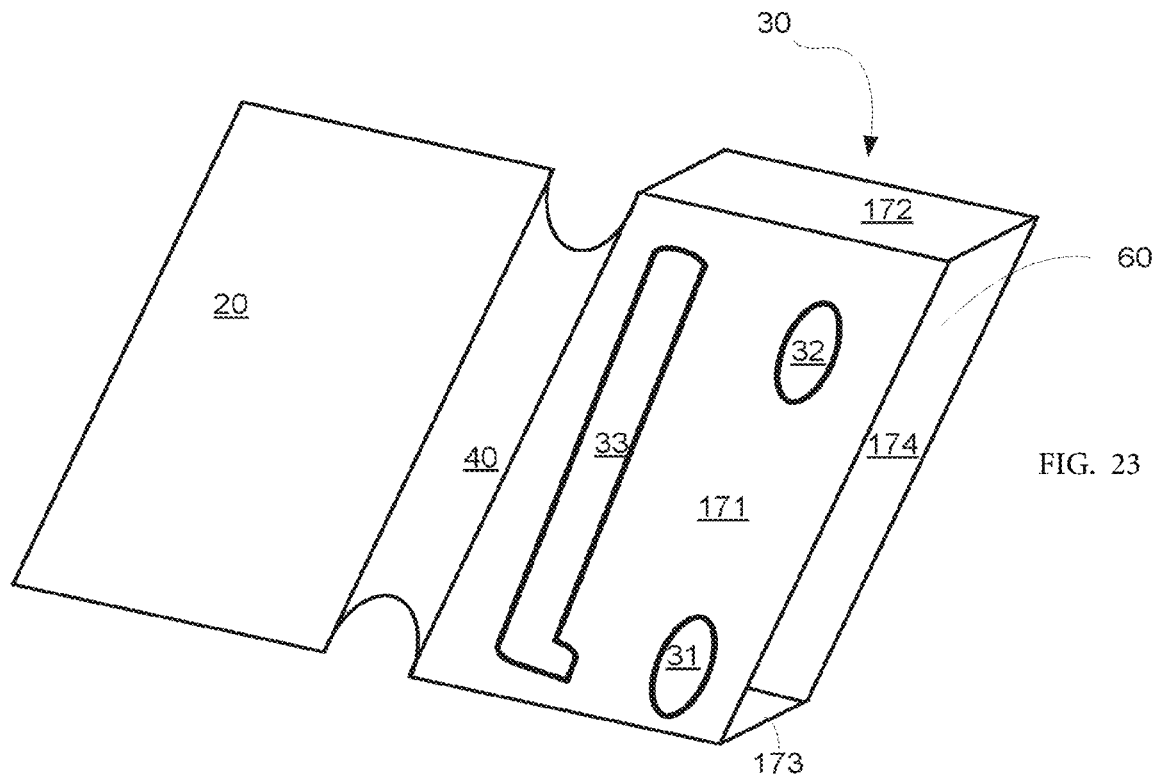

FIG. 23 is a side view (taken from the narrow dimension of the smartphone 100) of the jacket at an open position. The second portion 30 is positioned between the smartphone 100 and the first portion 20. FIG. 23 also shows interface 40, and both sides 111 and 112 of smartphone 100.

Figure 24:
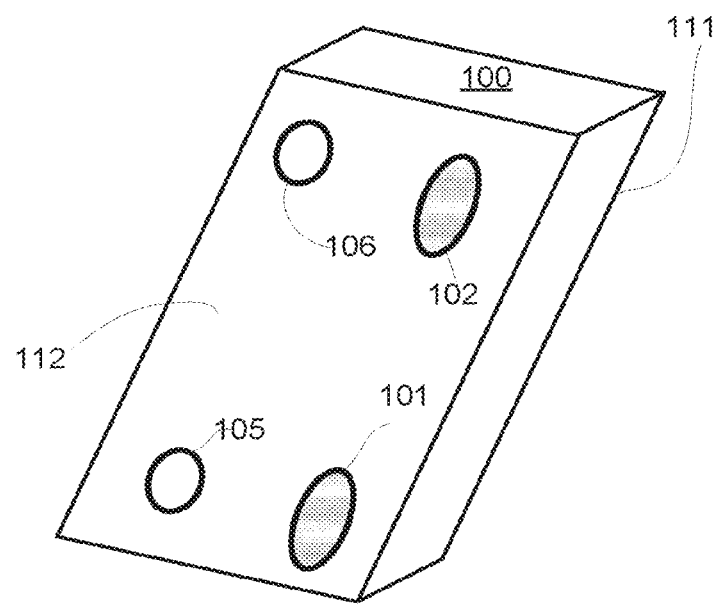

FIG. 24 illustrates a smartphone 100 and a jacket 10. The jacket has a first portion 20, an interface 40 and a second portion 30 that has sidewalls 171, 172, 173 and 174 that define an inner space 60 in which the smartphone 100 may be inserted. The inner space 60 may match the smartphone 100. The smartphone may be at least partially surrounded by the second portion 30 when inserted into the space.

Smartphone 100 of FIG. 24 is illustrated as including image sensors 105 and 106 (or illumination module and sensor) and electrodes 101 and 102.

Sidewall 171 includes electrodes 31, 32 as well as aperture 33 that match the locations of image sensors 105 and 106 and electrodes 101 and 102.

The matching means that once the smartphone is inserted into inner space 60—the electrodes 101 and 102 are contacted by electrodes 31 and 32 respectively and image sensors 105 and 106 are not concealed by aperture 33.

Smartphone 100 may be detached to inner space by detachment elements located in the inner space and/or outside the inner space. For example one or more laces may surround the smartphone (when inserted in the inner space) and may hold the smartphone within the inner space.

When the jacket is closed the electrodes 101 and 102 and image sensors 105 and 106 are protected.

The back panel 111 faces sidewall 174 and the front panel 112 may face sidewall 174.

Figure 25:
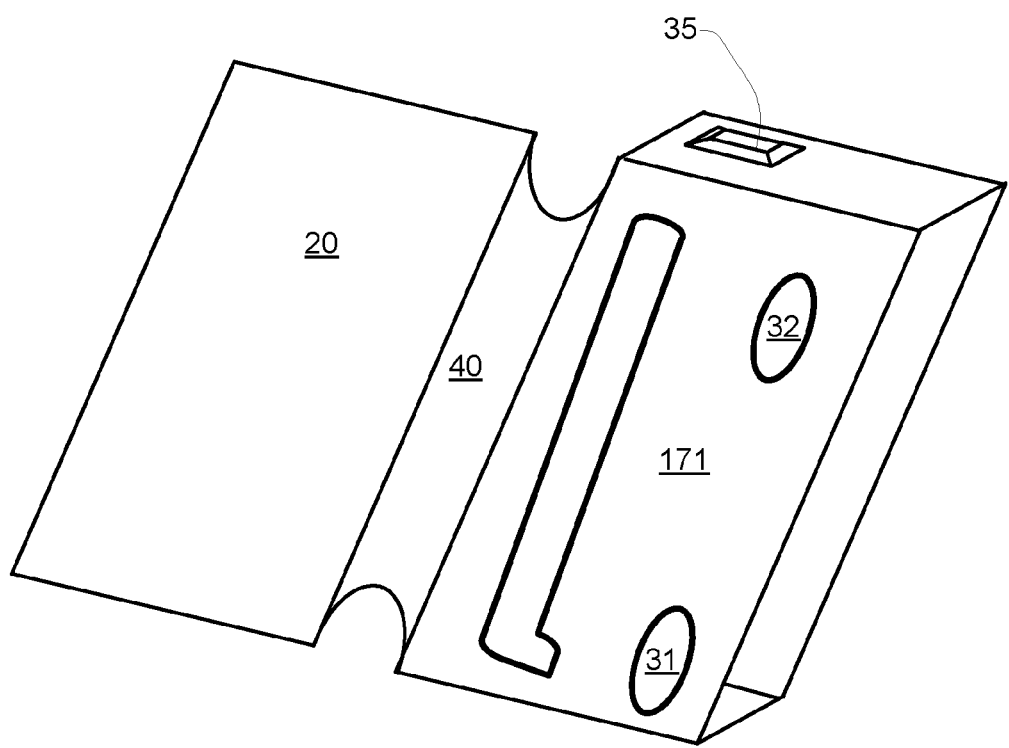

FIG. 25 illustrates a smartphone 100 and a jacket 10. The jacket has a first portion 20, an interface 40 and a second portion 30 that has sidewalls 171, 172, 173 and 174 that define an inner space 60 in which the smartphone 100 may be inserted. The jacket also includes thermometer 35.

Figure 26:
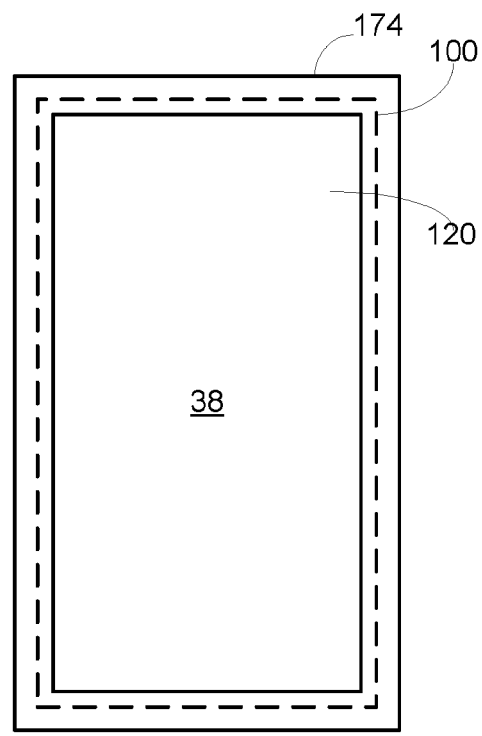
Figure 27:
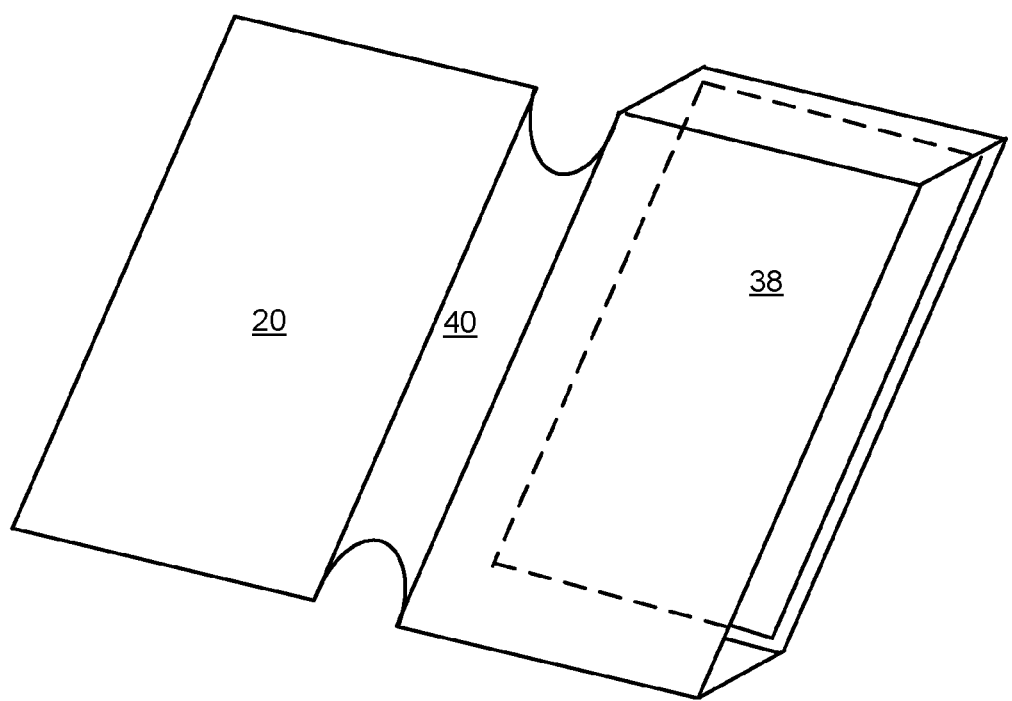

FIGS. 26 and 27 illustrate a screen 120 of a smartphone 100 that is aligned with window 38 of sidewall 174 so that most of the screen or the entire screen are not concealed by window 38. Window 38 may include a filtering element and/or a transparent protective shield.

Figure 28:
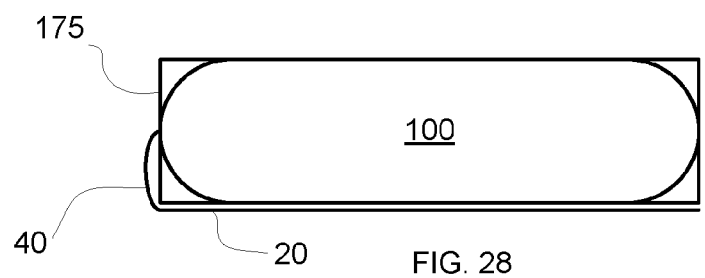
Figure 29:
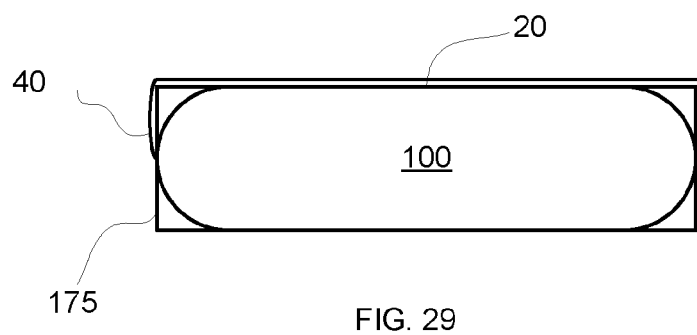
Figure 30:
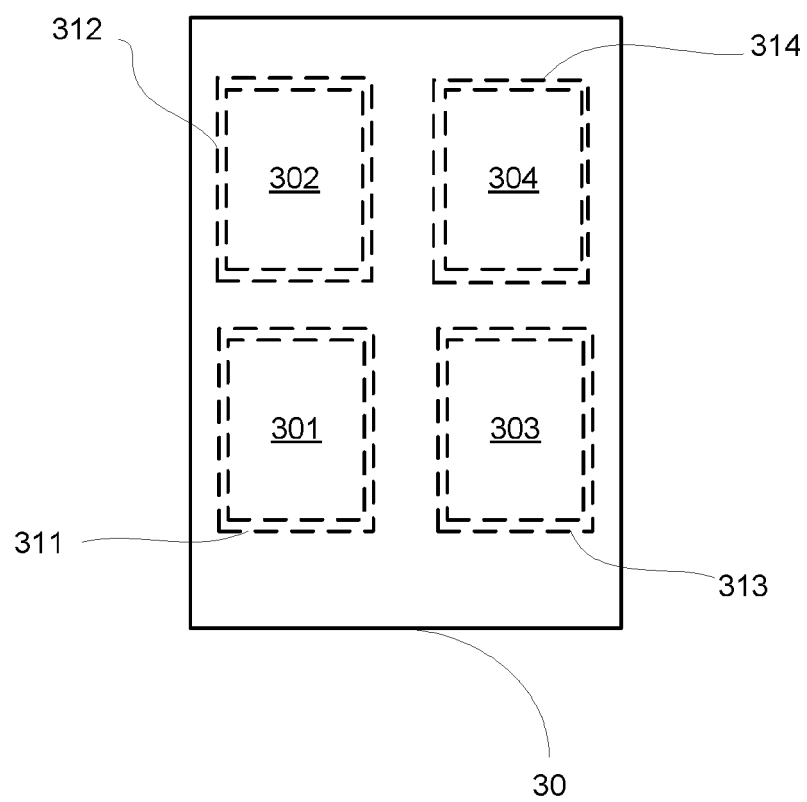

FIGS. 28 and 30 are side views (taken from the narrow dimension of the smartphone 100) of the jacket and the smartphone. Interface 40 is connected at the middle of sidewall 175 and may be moved between a position in which is conceals one sidewall of the jacket to another position in which it conceals the opposite sidewall of the jacket.

FIG. 30 illustrate the jacket as including pockets 311, 312, 313 and 314 in which medical modules 301, 302, 303 and 304 are placed.

Any combination of any elements illustrated in any of the previous figures may be provided.

The number of medical modules may differ from the number of medical members illustrated in each one of FIGS. 1-30. For example, the second portion may include any integer number of electrodes or may not include any electrodes.

The types of medical modules may differ from the types of medical members illustrated in each one of FIGS. 1-30.

The smartphone is merely an example of a computerized system especially a communication system. The computerized system may participate in processing data provided from the medical modules of the jacket, may merely transmit such the data and the like.

There may be provided a method for operating the one or more medical modules located within the jacket. The method may include positioning the jacket in an open position and performing medical measurements by the medical modules of the jacket.

Any reference to the term "comprising" or "having" should be interpreted also as referring to "consisting" of "essentially consisting of". For example—a method that comprises certain steps can include additional steps, can be limited to the certain steps or may include additional steps that do not materially affect the basic and novel characteristics of the method—respectively.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

Also for example, the examples, or portions thereof, may implemented as soft or code representations of physical circuitry or of logical representations convertible into physical circuitry, such as in a hardware description language of any appropriate type.

Also, the invention is not limited to physical devices or units implemented in non-programmable hardware but can also be applied in programmable devices or units able to perform the desired device functions by operating in accordance with suitable program code, such as mainframes, minicomputers, servers, workstations, personal computers, notepads, personal digital assistants, electronic games, automotive and other embedded systems, cell phones and various other wireless devices, commonly denoted in this application as 'computer systems'.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

I claim:

1. A jacket that comprises:
a first portion;
a second portion; and
an interface;
wherein the interface is movably coupled to the first portion and the second portion;
wherein the first portion comprises multiple medical modules, the multiple medical modules comprise at least one medical sensor and a physiological signal conduit for transferring a physiological signal from an inner side of the first portion to an exterior side of the first portion; wherein the physiological signal conduit comprises an outer surface located at the exterior side of the first portion and an inner surface located at the inner side; wherein the inner surface has a same size as a conductive interface of a mobile phone;
wherein the first and second portions are configured to be detachably coupled to the mobile phone;
wherein when the jacket is at a closed position then the first portion, the second portion and the interface define an inner space that is configured to receive the mobile phone and the first and second portions contact opposite sides of the mobile phone;
wherein when the jacket is at an open position, then the second portion contacts a back of the mobile phone, a first segment of the first portion contacts a sidewall of the mobile phone, a second segment of the first portion does not contact the mobile phone, the second segment is located to a side of the mobile phone, wherein an area of the second segment exceeds an area of the first segment; and
wherein when the jacket is at the open position, the first portion contacts the mobile phone and the second segment is rolled to a side of the mobile phone along an axis that is to the side of the mobile phone and above the mobile phone.

2. The jacket according to claim 1 wherein the physiological signal conduit is an electrode.

3. The jacket according to claim 1 wherein when the jacket is in the closed position the physiological signal conduit contacts the mobile phone.

4. The jacket according to claim 1 wherein the physiological signal conduit comprises an inner surface and an outer surface, wherein an area of the outer surface exceeds an area of the inner surface, wherein when the jacket is in the closed position the inner surface faces the inner space.

5. The jacket according to claim 1 comprising the physiological signal conduit and another physiological signal conduit, wherein the other physiological signal conduit comprises another inner surface and another outer surface, wherein when the jacket is in the closed position the inner surface and the other inner surface face the inner space.

6. The jacket according to claim 5 wherein an area of the other outer surface exceeds an area of the other inner surface.

7. The jacket according to claim 5 wherein a distance between the outer surface and the other outer surface exceeds a distance between the inner surface and the other inner surface.

8. The jacket according to claim 5 wherein the physiological signal conduit and the other physiological signal conduit are coupled to one or more signals processors of the multiple medical modules.

9. The jacket according to claim 1 wherein the multiple medical modules comprise a thermometer.

10. The jacket according to claim 1 wherein the multiple medical modules comprise an analyzer that is configured to analyze a medical sample conveyed on a conveyor, wherein the jacket comprises slot for receiving the conveyor.

11. The jacket according to claim 1 wherein at least one of the first and second portions is configured to partially surround the mobile phone.

12. The jacket according to claim 1 wherein the first and second portions comprise apertures that correspond to a location of images sensors of the mobile phone.

13. The jacket according to claim 1 wherein when the jacket is at the closed position, the medical modules contact the mobile phone.

14. The jacket according to claim 1 wherein a width of the physiological signal conduit gradually changes within the first portion.

15. The jacket according to claim 1 comprising a slot for receiving sampling elements with a sampled body fluid.

16. A jacket that comprises:
a first portion;
a second portion; and
an interface;
wherein the first and second portions are movably coupled to the interface and are configured to move along an axis of rotation that is parallel to a longitude axis of a mobile phone between (a) a close position in which the first and second portions are spaced apart from each other and are ordered in a first order, and (b) an open position in which the first and second portions contact each other and are ordered in a second order that is opposite to the first order;
wherein the first portion comprises multiple medical modules;
wherein the first and second portions are configured to be detachably coupled to a mobile phone;
wherein when positioned in the closed position the first portion, the second portion and the interface define an inner space that is configured to receive a mobile phone, and wherein when positioned at an open position a majority of the second portion is located to a side of the first portion and is rolled along an axis that is located to a side of the first portion.

17. The jacket according to claim 14 wherein at least one of the first and second portions is configured to partially surround the mobile phone.

18. The jacket according to claim 16 wherein the multiple medical modules comprise at least one medical sensor and a physiological signal conduit for transferring a physiological signal from an inner side of the first portion to an exterior side of the first portion.

19. The jacket according to claim 18 wherein the physiological signal conduit comprises an outer surface located at the exterior side of the first portion and an inner surface located at the inner side.

20. The jacket according to claim 18 wherein the physiological signal conduit is an electrode.

21. The jacket according to claim 18 wherein when the jacket is in the closed position the physiological signal conduit contacts the mobile phone.

22. The jacket according to claim 18 comprising the physiological signal conduit and another physiological signal conduit, wherein the other physiological signal conduit comprises another inner surface and another outer surface, wherein when the jacket is in the closed position the inner surface and the other inner surface face the inner space.

23. The jacket according to claim 18 wherein the multiple medical modules comprise a thermometer.

24. The jacket according to claim 18 wherein the multiple medical modules comprise an analyzer that is configured to analyze a medical sample conveyed on a conveyor, wherein the jacket comprises slot for receiving the conveyor.

* * * * *